(12) United States Patent
Hacker et al.

(10) Patent No.: US 8,785,350 B2
(45) Date of Patent: Jul. 22, 2014

(54) HERBICIDAL COMPOSITIONS FOR TOLERANT OR RESISTANT SOYBEAN CROPS

(75) Inventors: Erwin Hacker, Langenenslingen-Friedlingen (DE); Hansjörg Dietrich, Liederbach am Taunus (DE); Klaus Trabold, Heidelberg (DE); Elmar Gatzweiler, Bad Nauheim (DE); Frank Ziemer, Kriftel (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/473,935

(22) Filed: May 17, 2012

(65) Prior Publication Data
US 2013/0023413 A1    Jan. 24, 2013

Related U.S. Application Data

(60) Provisional application No. 61/488,978, filed on May 23, 2011.

(30) Foreign Application Priority Data

May 20, 2011 (EP) ...................... 11166986

(51) Int. Cl.
*A01N 57/00*    (2006.01)
(52) U.S. Cl.
USPC .......................... 504/127; 504/126
(58) Field of Classification Search
CPC combination set(s) only.
See application file for complete search history.

(56) References Cited

U.S. PATENT DOCUMENTS

| 4,168,963 | A  | 9/1979 | Rupp et al. |
| 7,105,470 | B1 | 9/2006 | Hacker et al. |
| 2007/0179059 | A1 | 8/2007 | Epp et al. |
| 2007/0179060 | A1 | 8/2007 | Balko et al. |
| 2009/0062121 | A1 | 3/2009 | Satchivi et al. |

FOREIGN PATENT DOCUMENTS

| DE | 27 17 440 | 12/1971 |
| WO | 2007082098 | 7/2007 |
| WO | WO-2007082098 | * 7/2007 |
| WO | 2009029518 | 3/2009 |

* cited by examiner

*Primary Examiner* — Alton Pryor
(74) *Attorney, Agent, or Firm* — Miles & Stockbridge, P.C.

(57) ABSTRACT

The invention provides herbicide combinations and provides for the use of herbicide combinations for control of weeds in soybean and leguminous species, wherein the particular herbicide combination comprises (A) a herbicide from the group of compounds of the formula (A1)

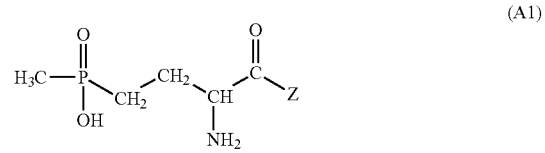

(A1)

in which Z is hydroxyl, —NHCH(CH$_3$)CONHCH(CH$_3$)COOH or —NHCH(CH$_3$)CONHCH[CH$_2$CH(CH$_3$)$_2$]COOH,
or esters or salts thereof,
(B) a herbicide of the formula (B1)

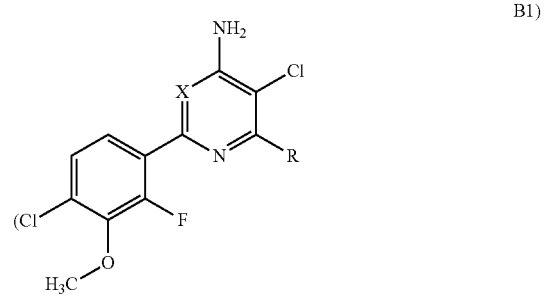

B1)

in which X is N or CH and R is CO$_2$H or a herbicide-active derivative, and the soybean and leguminous species are tolerant to the herbicides (A) and (B) present in the combination, optionally in the presence of safeners.

18 Claims, No Drawings

HERBICIDAL COMPOSITIONS FOR TOLERANT OR RESISTANT SOYBEAN CROPS

CROSS REFERENCE TO RELATED APPLICATIONS

This application claims the priority to European Patent Application No. 11166986.7, filed May 20, 2011, and U.S. Provisional Application No. 61/488,978 filed May 23, 2011, the content of both of which are incorporated herein by reference in their entirety.

BACKGROUND

1. Field of the Invention

The invention lies in the field of crop protection compositions which can be used against weeds in tolerant or resistant crops of soybeans and other leguminous species, for example beans, peas and lentils, and comprise, as active herbicidal ingredients, a combination of two or more herbicides.

2. Description of Related Art

The introduction of tolerant or resistant soybean and leguminous species and lines, especially of transgenic soybean and leguminous species and lines, supplements the conventional weed control system with novel active ingredients which are non-selective per se in conventional soybean and leguminous species. The active ingredients are, for example, known broad spectrum herbicides such as glyphosate, sulfosate, glufosinate, bialaphos and imidazolinone herbicides, which can now be used in the crops which have been developed to be tolerant to each of them. The efficacy of these herbicides against weeds in the tolerant crops is at a high level, but—similarly to other herbicide treatments—depends on the nature of the herbicide used, the application rate thereof, the respective formulation form, the weeds to be controlled in each case, the climatic and soil conditions, etc. In addition, the herbicides have weaknesses (gaps) with respect to specific species of weeds. A further criterion is the duration of action or the degradation rate of the herbicide. Attention should also be paid to any changes in the sensitivity of weeds which can occur in the case of prolonged use of the herbicides or in a geographically limited manner. Losses of action in the case of individual plants can be balanced out only to a relative degree, if at all, by higher application rates of the herbicides. Moreover, there is still a need for methods of achieving the herbicidal action with a lower application rate of active ingredients.

One means of improving the use profile of a herbicide may consist in the combination of the active ingredient with one or more other active ingredients which contribute the desired additional properties. However, in the case of the combined use of several active ingredients, it is not a rare event for phenomena of chemical, physical and biological incompatibility to occur, for example inadequate stability of a coformulation, decomposition of an active ingredient or antagonism of the biological action of the active ingredients. In contrast, desirable combinations of active ingredients are those with a favorable action profile (action level, compatibility), high stability and possible synergistic enhancement of action, which allows reduction of the application rate compared to the individual application of the active ingredients to be combined.

SUMMARY

It has now been found that, surprisingly, particular active ingredients from the group of the broad spectrum herbicides (A) mentioned, in combination with particular herbicides (B), interact in a particularly favorable (synergistic) manner when they are used in soybean and leguminous species suitable for selective use of the former herbicides.

The invention thus provides for the use of herbicide combinations for control of weeds in soybean crops, wherein the particular herbicide combination comprises (A) a herbicide from the group of compounds of the formula (A1)

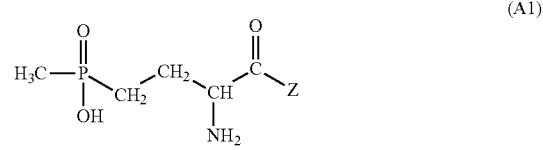

(A1)

in which Z is hydroxyl, —NHCH($CH_3$)CONHCH($CH_3$)COOH or —NHCH($CH_3$)CONHCH[$CH_2$CH($CH_3$)$_2$]COOH, or esters or salts thereof, (B) a herbicide of the formula (B1)

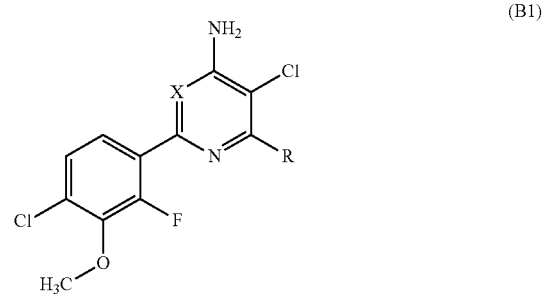

(B1)

in which X is N or CH and R is $CO_2$H or a herbicide-active derivative, and the soybean and leguminous species are tolerant to the herbicides (A) and (B) present in the combination, optionally in the presence of safeners.

DETAILED DESCRIPTION OF A PREFERRED EMBODIMENT

The compounds (A) and (B) are known. Compounds of the (A1) type are described, for example, in DE-A 2717440. Compounds of the (B1) type are described, for example, in WO 2007/082098. Mixtures of these compounds with other herbicides are described, for example, in WO 2009/029518. Also described therein are synergistic mixtures of some of the inventive (B) components with the total herbicide glyphosate, but not the use thereof in tolerant crops, but rather merely synergism in relation to herbicidal action against weed grasses/broad-leaved weeds.

Preferred components (A) are, in each case alone,
glufosinate and salts thereof,
L-glufosinate and salts thereof and
bialaphos and salts thereof.

Particularly preferred components (A) are, in each case alone,
glufosinate-ammonium (A1.1),
L-glufosinate-ammonium (A1.2) and
bialaphos-sodium (A1.3).

Compounds of the formula (B1) in which the substituent R is $CO_2H$ (i.e. carboxylic acid function) are assumed to be those compounds which bind to the active site of a plant enzyme or of a receptor and thus cause a herbicidal effect in the plant. Other compounds of the formula (B1) in which the substituent R is a group which can be converted to a carboxylic acid function (i.e. COM) within plants or the environment generate a similar herbicidal effect and are likewise encompassed by the present invention. Thus, in the context of the present invention, a herbicidally active derivative is understood to mean especially salts, esters, carboxamides, acyl hydrazides, imidates, thioimidates, amidines, acyl halides, acyl cyanides, acid anhydrides, ethers, acetals, orthoesters, carboxaldehydes, oximes, hydrazones, thio acids, thio esters, dithiol esters, nitriles and any other carboxylic acid derivative which does not extinguish the herbicidal action of the compound of the formula (B1) and, in plants and/or in the soil, for example through hydrolysis, oxidation, reduction or another kind of metabolization, provides the carboxylic acid function which, according to pH, is present in dissociated or undissociated form.

The compounds of the formula (B1) may additionally form salts through addition of a suitable inorganic or organic acid, for example HCl, HBr, $H_2SO_4$ or $HNO_3$, but also oxalic acid or sulfonic acids, onto a basic group, for example amino or alkylamino. Suitable substituents present in deprotonated form, for example sulfonic acids or carboxylic acids, can form internal salts with groups which are themselves protonatable, such as amino groups. Salts can likewise be formed by replacing the hydrogen in suitable substituents, for example sulfonic acids or carboxylic acids, with a cation suitable for agriculture. These salts are, for example, metal salts, especially alkali metal salts or alkaline earth metal salts, especially sodium and potassium salts, or else ammonium salts, salts with organic amines or quaternary ammonium salts with cations of the formula $[NRR'R''R''']^+$, in which R to R''' are each independently an organic radical, especially alkyl, aryl, aralkyl or alkylaryl.

More particularly, the compounds of the formula (B1) may also include N-oxides. Corresponding pyridine N oxides are obtainable via an oxidation of the corresponding pyridines. Suitable oxidation methods are described, for example, in Houben-Weyl, Methoden der organischen Chemie [Methods of Organic Chemistry], supplementary and additional volumes to the 4th edition, Volume E 7b, p. 565 ff.

Preferred components (B) are, in each case alone:
4-amino-3-chloro-6-(4-chloro-2-fluoro-3-methoxyphenyl)pyridine-2-carboxylic acid (B1.0),
methyl 4-amino-3-chloro-6-(4-chloro-2-fluoro-3-methoxyphenyl)pyridine-2-carboxylate (B1.1),
ethyl 4-amino-3-chloro-6-(4-chloro-2-fluoro-3-methoxyphenyl)pyridine-2-carboxylate (B1.2),
n-propyl 4-amino-3-chloro-6-(4-chloro-2-fluoro-3-methoxyphenyl)pyridine-2-carboxylate (B1.3),
i-propyl 4-amino-3-chloro-6-(4-chloro-2-fluoro-3-methoxyphenyl)pyridine-2-carboxylate (B1.4),
n-butyl 4-amino-3-chloro-6-(4-chloro-2-fluoro-3-methoxyphenyl)pyridine-2-carboxylate (B1.5),
2-butyl 4-amino-3-chloro-6-(4-chloro-2-fluoro-3-methoxyphenyl)pyridine-2-carboxylate (B1.6),
tert-butyl 4-amino-3-chloro-6-(4-chloro-2-fluoro-3-methoxyphenyl)pyridine-2-carboxylate (B1.7),
allyl 4-amino-3-chloro-6-(4-chloro-2-fluoro-3-methoxyphenyl)pyridine-2-carboxylate (B1.8),
2-butoxyethyl 4-amino-3-chloro-6-(4-chloro-2-fluoro-3-methoxyphenyl)pyridine-2-carboxylate (B1.9),
4-amino-3-chloro-6-(4-chloro-2-fluoro-3-methoxyphenyl)pyridine-2-carboxylic acid triethylammonium salt (B1.10)
4-amino-3-chloro-6-(4-chloro-2-fluoro-3-methoxyphenyl)pyridine-2-carboxylic acid potassium salt (B1.11)
6-amino-5-chloro-2-(4-chloro-2-fluoro-3-methoxyphenyl)pyrimidine-4-carboxylic acid (B1.12)
methyl 6-amino-5-chloro-2-(4-chloro-2-fluoro-3-methoxyphenyl)pyrimidine-4-carboxylate (B1.13)
ethyl 6-amino-5-chloro-2-(4-chloro-2-fluoro-3-methoxyphenyl)pyrimidine-4-carboxylate (B1.14)
n-propyl 6-amino-5-chloro-2-(4-chloro-2-fluoro-3-methoxyphenyl)pyrimidine-4-carboxylate (B1.15)
i-propyl 6-amino-5-chloro-2-(4-chloro-2-fluoro-3-methoxyphenyl)pyrimidine-4-carboxylate (B1.16)
n-butyl 6-amino-5-chloro-2-(4-chloro-2-fluoro-3-methoxyphenyl)pyrimidine-4-carboxylate (B1.17)
2-butyl 6-amino-5-chloro-2-(4-chloro-2-fluoro-3-methoxyphenyl)pyrimidine-4-carboxylate (B1.18)
tert-butyl 6-amino-5-chloro-2-(4-chloro-2-fluoro-3-methoxyphenyl)pyrimidine-4-carboxylate (B1.19)
allyl 6-amino-5-chloro-2-(4-chloro-2-fluoro-3-methoxyphenyl)pyrimidine-4-carboxylate (B1.20)
2-butoxyethyl 6-amino-5-chloro-2-(4-chloro-2-fluoro-3-methoxyphenyl)pyrimidine-4-carboxylate (B1.21)
6-amino-5-chloro-2-(4-chloro-2-fluoro-3-methoxyphenyl)pyrimidine-4-carboxylic acid triethylammonium salt (B1.22) and
6-amino-5-chloro-2-(4-chloro-2-fluoro-3-methoxyphenyl)pyrimidine-4-carboxylic acid potassium salt (B1.23).

Particularly preferred components (B) are
4-amino-3-chloro-6-(4-chloro-2-fluoro-3-methoxyphenyl)pyridine-2-carboxylic acid (B1.0) and
methyl 4-amino-3-chloro-6-(4-chloro-2-fluoro-3-methoxyphenyl)pyridine-2-carboxylate (B1.1).

In another embodiment, particularly preferred components (B) are
6-amino-5-chloro-2-(4-chloro-2-fluoro-3-methoxyphenyl)pyrimidine-4-carboxylic acid (B1.12) and
methyl 6-amino-5-chloro-2-(4-chloro-2-fluoro-3-methoxyphenyl)pyrimidine-4-carboxylate (B1.13).

The synergistic effects are observed on combined deployment of the active ingredients (A) and (B), but can also be found in the case of application at different times (splitting). It is also possible to apply the herbicides or the herbicide combinations in several portions (sequential application), for example after pre-emergence applications, followed by post-emergence applications, or after early post-emergence applications, followed by applications at the middle or late post-emergence stage. Preference is given to the simultaneous application of the active ingredients of the respective combination, optionally in several portions. However, the application of the individual active ingredients of a combination at different times is possible and may be advantageous in the individual case. It is also possible to integrate other crop protection compositions into this system application, such as fungicides, insecticides, acaricides, etc., and/or various assistants, adjuvants and/or fertilizer administrations.

The synergistic effects allow a reduction in the application rates of the individual active ingredients, a higher intensity of action against the same weed species at the same application rate, the control of species which have not been covered to date (gaps), an extension of the application period and/or a reduction in the number of individual applications necessary and—as a result for the user—more economically and ecologically advantageous weed control systems.

For example, the inventive combinations of (A)+(B) enable synergistic enhancements of action, which unexpectedly go well beyond the effects which are achieved with the individual active ingredients (A) and (B).

According to the invention, herbicide combinations which can be used particularly favorably in tolerant soybean and leguminous species are provided.

The herbicides (A1.1) to (A1.3) mentioned are absorbed via the green parts of the plants and are known as broad spectrum herbicides or total herbicides; they are inhibitors of the enzyme glutamine synthetase in plants; see "The Pesticide Manual" 11th Edition, British Crop Protection Council 1997, p. 643-645 and 120-121.

In the inventive combinations, using the example of the racemate of glufosinate, an application rate in the range from 12.5 to 2500 g AS/ha (=grams of active substance per hectare) is generally required, preferably 25 to 2500 g AS/ha, more preferably 50-1500 g AS/ha. Corresponding amounts converted to moles per hectare also apply to (A1.1), (A1.2) and (A1.3).

The combinations are appropriately used in soybean and leguminous species which are tolerant to the compounds (A1). The tolerance may have been generated by breeding or mutation selection, or else by recombinant methods. Some tolerant soybean crops which have been produced by genetic engineering are already known and are being used in practice; cf. article in the journal "Zuckerrübe", volume 47 (1998), p. 217 ff.; for production of transgenic plants resistant to glufosinate; see EP-A-0 242 246, EP-A-0 242 236, EP-A-0 257 542, EP-A-0 275 957, EP-A-0 513 054).

Legumes are selected, for example, from the group consisting of peas, for example field peas (*Pisum sativum* L. convar. *speciosum*), garden peas (*Pisum sativum* L. convar. *sativum*), wrinkled peas (*Pisum sativum* L. convar. *medullar*, Alef.) and snow peas (*Pisum sativum* L. convar. *axiphium* Alef.); chickpeas, for example *Cicer arietinum* fo. *Album*, *Cicer arietinum* fo. *Fuscum*, *Cicer arietinum* fo. *Macrospermum*, *Cicer arietinum* fo.; beans, for example moth bean (*Vigna aconitifolia*), adzuki bean (*Vigna angulari*), urd bean (*Vigna mungo*), mung bean (*Vigna radiata*), bambara groundnut (*Vigna subterranea*), rice bean (*Vigna umbellata*), catjang bean (*Vigna unguiculata* subsp. *cylindrica* (L.)), asparagus bean (*Vigna unguiculata* subsp. *sesquipedalis*), blackeye bean (*Vigna unguiculata* (L.) Walp. subsp. *unguiculata*), guar bean (*Cyamopsis tetragonolobus* (L.) Taub.), kidney bean (*Phaseolus vulgaris* L.), lima bean, butter bean (*Phaseolus lunatus* L.), tepary bean (*Phaseolus acutifolius*), scarlet runner bean (*Phaseolus coccineus* L.), field bean (*Vicia faba*); and lentils, for example green lentils, red lentils, mountain lentils, beluga lentils, puy lentils and yellow lentils.

The application rates of the herbicides (B) may vary greatly. The following are appropriate ranges:

Generally 2.5-500 g AS/ha, preferably 4 to 400 g AS/ha, more preferably 5-250 g AS/ha (cf. the figures for the group of compounds (A)).

The ratios of compounds (A) and (B) are calculated from the application rates mentioned for the individual substances.

Of particular interest is the use of each individual combination of those listed in the following table.

TABLE 1

| No. | Active ingredient (A) | Active ingredient (B) |
| --- | --- | --- |
| 1 | A1.1 | B1.0 |
| 2 | A1.1 | B1.1 |
| 3 | A1.1 | B1.2 |
| 4 | A1.1 | B1.3 |

TABLE 1-continued

| No. | Active ingredient (A) | Active ingredient (B) |
| --- | --- | --- |
| 5 | A1.1 | B1.4 |
| 6 | A1.1 | B1.5 |
| 7 | A1.1 | B1.6 |
| 8 | A1.1 | B1.7 |
| 9 | A1.1 | B1.8 |
| 10 | A1.1 | B1.9 |
| 11 | A1.1 | B1.10 |
| 12 | A1.1 | B1.11 |
| 13 | A1.1 | B1.12 |
| 14 | A1.1 | B1.13 |
| 15 | A1.1 | B1.14 |
| 16 | A1.1 | B1.15 |
| 17 | A1.1 | B1.16 |
| 18 | A1.1 | B1.17 |
| 19 | A1.1 | B1.18 |
| 20 | A1.1 | B1.19 |
| 21 | A1.1 | B1.20 |
| 22 | A1.1 | B1.21 |
| 23 | A1.1 | B1.22 |
| 24 | A1.1 | B1.23 |
| 25 | A1.2 | B1.0 |
| 26 | A1.2 | B1.1 |
| 27 | A1.2 | B1.2 |
| 28 | A1.2 | B1.3 |
| 29 | A1.2 | B1.4 |
| 30 | A1.2 | B1.5 |
| 31 | A1.2 | B1.6 |
| 32 | A1.2 | B1.7 |
| 33 | A1.2 | B1.8 |
| 34 | A1.2 | B1.9 |
| 35 | A1.2 | B1.10 |
| 36 | A1.2 | B1.11 |
| 37 | A1.2 | B1.12 |
| 38 | A1.2 | B1.13 |
| 39 | A1.2 | B1.14 |
| 40 | A1.2 | B1.15 |
| 41 | A1.2 | B1.16 |
| 42 | A1.2 | B1.17 |
| 43 | A1.2 | B1.18 |
| 44 | A1.2 | B1.19 |
| 45 | A1.2 | B1.20 |
| 46 | A1.2 | B1.21 |
| 47 | A1.2 | B1.22 |
| 48 | A1.2 | B1.23 |
| 49 | A1.3 | B1.0 |
| 50 | A1.3 | B1.1 |
| 51 | A1.3 | B1.2 |
| 52 | A1.3 | B1.3 |
| 53 | A1.3 | B1.4 |
| 54 | A1.3 | B1.5 |
| 55 | A1.3 | B1.6 |
| 56 | A1.3 | B1.7 |
| 57 | A1.3 | B1.8 |
| 58 | A1.3 | B1.9 |
| 59 | A1.3 | B1.10 |
| 60 | A1.3 | B1.11 |
| 61 | A1.3 | B1.12 |
| 62 | A1.3 | B1.13 |
| 63 | A1.3 | B1.14 |
| 64 | A1.3 | B1.15 |
| 65 | A1.3 | B1.16 |
| 66 | A1.3 | B1.17 |
| 67 | A1.3 | B1.18 |
| 68 | A1.3 | B1.19 |
| 69 | A1.3 | B1.20 |
| 70 | A1.3 | B1.21 |
| 71 | A1.3 | B1.22 |
| 72 | A1.3 | B1.23 |

In individual cases, it may be advisable to combine one or more of compounds (A) with two or more compounds (B).

In addition, the inventive combinations can be used together with other active ingredients, for example from the group of the fungicides, insecticides and crop growth regulators, or from the group of additives and formulation assistants customary in crop protection. Additives are, for example, fertilizers, dyes, oils and ionic/nonionic wetting agents.

Also in accordance with the invention are those combinations which also comprise one or more further active ingredients of other structures [active ingredients (C)], for example safeners, crop growth regulators or further herbicides. For combinations of the latter type comprising three or more active ingredients, the preferred conditions explained for inventive two-substance combinations likewise apply primarily, provided that the inventive two-substance combinations are present therein and with regard to the two-substance combination in question. When the soybean and leguminous species do not have natural tolerance to the active ingredient (C), such a tolerance must be produced by mutation selection, breeding or by genetic engineering methods, in order to enable inventive uses.

Suitable active ingredients (C) are, for example, the safeners benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, "AD-67" or "MON 4660" (=3-dichloroacetyl-1-oxa-3-aza-spiro[4,5]decane), "TI-35" (=1-dichloroacetylazepane), "dimepiperate" or "MY-93" (=S-1-methyl-1-phenylethyl piperidine-1-thiocarboxylate), "daimuron" or "SK 23" (=1-(1-methyl-1-phenylethyl)-3-p-tolylurea) or "cumyluron"="JC-940" (=3-(2-chlorophenylmethyl)-1-(1-methyl-1-phenylethyl)urea) or the following herbicides and plant growth regulators:

acetochlor, acibenzolar, acibenzolar-5-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryn, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]-ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glyphosate, glyphosate-diammonium, glyphosate-isopropylammonium, glyphosate-potassium, H-9201, i.e. O-(2,4-dimethyl-6-nitrophenyl) O-ethyl isopropylphosphoroamidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropen, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron-ester, monuron, MT-128, i.e. 6-chloro-N-[(2E)-3-chloroprop-2-en-1-yl]-5-methyl-N-phenylpyridazin-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, profluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron (KIH 485), pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl-5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and also the following compounds:

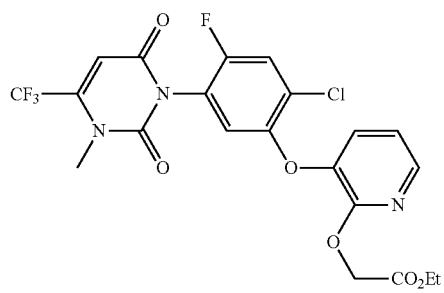

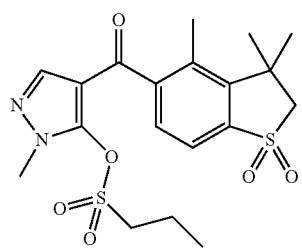

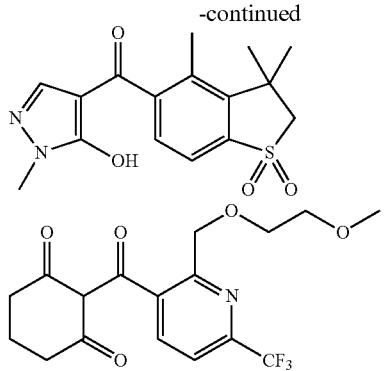

In the case of HPPD inhibitor-tolerant soybean and leguminous species, it is also possible to add HPPD inhibitors, for example mesotrione, sulcotrione bicyclopyrone, pyrasulfotole, tembotrione/topramezone or isoxaflutole as active ingredients (C).

Particularly suitable active ingredients (C) are (C1) herbicides with selective action in soybeans against monocotyledonous and predominantly dicotyledonous weeds and have foliar action and/or soil action (residual action), such as (C1.1) trifluralin (Pesticide Manual (PM), p. 1248-1250) (250 to 5000 g AS/ha, especially 400 to 4000 g AS/ha), (C1.2) metribuzin (PM, p. 840-841) (250 to 4000 g AS/ha, especially 500 to 3000 g AS/ha), (C1.3) clomazone (PM, p. 256-257) (150 to 5000 g AS/ha, especially 200 to 3000 g AS/ha), (C1.4) pendimethalin (PM, p. 937-939) (250 to 4000 g AS/ha, especially 500 to 3000 g AS/ha), (C1.5) metolachlor (PM, p. 833-834), also in the optically active form S-metolachlor (100 to 5000 g AS/ha, especially 200 to 4000 g AS/ha), (C1.6) flumetsulam (PM, p. 573-574) (5 to 300 g AS/ha, especially 10 to 100 g AS/ha), (C1.7) dimethenamid (CAS RN: 87674-68-8)/Dimethenamid-p (CAS RN: 163515-14-8)(PM, p. 409-410) (20 to 5000 g AS/ha, especially 50 to 4000 g AS/ha), (C1.8) alachlor (PM, p. 23-24) (250 to 5000 g AS/ha, especially 500 to 4000 g AS/ha), (C1.9) linuron (PM, p. 751-753) (250 to 5000 g AS/ha, especially 500 to 4000 g AS/ha), (C1.10) sulfentrazone (PM, p. 1126-1127) (50 to 2000 g AS/ha, especially 70 to 1500 g AS/ha), (C1.11) ethalfluralin (PM, p. 473-474) (250 to 5000 g AS/ha, especially 500 to 4000 g AS/ha), (C1.12) fluthiamide (BAY FOE 5043, Flufenacet) (PM, p. 82-83) (50 to 5000 g AS/ha, especially 70 to 4000 g AS/ha), (C1.13) norflurazon (PM, p. 886-888), (500 to 5000 g AS/ha, especially 750 to 4000 g AS/ha), (C1.14) vernolate (PM, p. 1264-1266), (250 to 5000 g AS/ha, especially 500 to 4000 g AS/ha) and/or optionally (C1.15) flumioxazin (PM, p. 576-577), (10 to 500 g AS/ha, especially 20 to 400 g AS/ha) and/or (C1.16) imazapyr (CAS RN: 81334-34-1), also has imazapyr-isopropylammonium (50 to 5000 g AS/ha, especially 80 to 3000 g AS/ha), (C1.17) imazamox (CAS RN: 114311-32-9) also has imazamox-ammonium (1 to 150 g AS/ha, especially 2 to 100 g AS/ha), (C1.18) imazaquin (CAS RN: 81335-37-7) also has imazaquin-ammonium (2 to 300 g AS/ha, especially 4 to 200 g AS/ha) and/or (C. 1.19) diflufenzopyr (CAS RN: 109293-97-2); (10 to 400 g AS/ha, especially 20 to 300 g AS/ha), (C. 1.20) carfentrazone (CAS RN: 128621-72-7); (1 to 100 g AS/ha, especially 3 to 80 g AS/ha);

(C. 1.21) imazethapyr (CAS RN: 81335-77-5)/ Imazethapyr-ammonium (5 to 300 g AS/ha, especially 10 to 200 g AS/ha);

(C. 1.22) dicamba (CAS RN: 1918-00-9); (10 to 800 g AS/ha, especially 20 to 600 g AS/ha)

(C. 1.23) mesotrione (CAS RN: 104206-82-8); (5 to 500 g AS/ha, especially 10 to 300 g AS/ha)

(C. 1.24) bicyclopyrone (CAS RN: 352010-68-5); (5 to 500 g AS/ha, especially 10 to 300 g AS/ha)

(C. 1.26) pyrasulfutole (CAS RN: 365400-11-9); (3 to 300 g AS/ha, especially 5 to 200 g AS/ha)

(C. 1.27) tembotrione (CAS RN: 335104-84-2); (5 to 500 g AS/ha, especially 10 to 300 g AS/ha)

(C. 1.28) isoxaflutole (CAS RN: 141112-29-0); (5 to 500 g AS/ha, especially 10 to 300 g AS/ha)

(C. 1.29) sulcotrione (CAS RN: 99105-77-8); (20 to 1000 g AS/ha, especially 30 to 800 g AS/ha)

(C. 1.30) topramezone (CAS RN: 210631-68-8); (1 to 300 g AS/ha, especially 2 to 200 g AS/ha)

(C2) herbicides with selective action in soybeans against dicotyledonous weeds, for example (C2.1) chlortoluron, chlorotoluron (PM, p. 229-231) (250 to 5000 g AS/ha, especially 500 to 4000 g AS/ha), (C2.2) bentazone (PM, p. 109-111) (250 to 5000 g AS/ha, especially 500 to 4000 g AS/ha), (C2.3) thifensulfuron and esters thereof, especially the methyl ester (PM, p. 1188-1190) (1 to 120 g AS/ha, especially 2 to 90 g AS/ha), (C2.4) oxyfluorfen (PM, p. 919-921) (40 to 800 g AS/ha, especially 60 to 600 g AS/ha), (C2.5) lactofen (PM, p. 747-748) (20 to 400 g AS/ha, especially 30 to 300 g AS/ha), (C2.6) fomesafen (PM, p. 616-618) (250 to 5000 g AS/ha, especially 500 to 4000 g AS/ha), (C2.7) flumiclorac (PM, p. 575-576) and esters thereof, such as the pentyl ester (10 to 400 g AS/ha, especially 20 to 300 g AS/ha), (C2.8) acifluorfen and the sodium salt thereof (PM, p. 12-14) (40 to 800 g AS/ha, especially 60 to 600 g AS/ha), (C2.9) 2,4-DB (PM, p. 337-339) and esters and salts thereof (250 to 5000 g AS/ha, especially 500 to 4000 g AS/ha) and/or (C2.10) 2,4-D (PM, p. 323-327) and esters and salts thereof (250 to 5000 g AS/ha, especially 500 to 4000 g AS/ha) and/or optionally (C2.11) chlorimuron and salts and esters such as chlorimuron-ethyl (PM, p. 217-218) (200 to 4000 g AS/ha, especially 500 to 3000 g AS/ha), (C2.12) cloransulam and salts and esters thereof such as cloransulam-methyl (PM, p. 265) (1 to 150 g AS/ha, especially 3 to 120 g AS/ha), (C2.13) diclosulam (cf. AG CHEM New Compound Review, Vol. 17, (1999) page 37, triazolopyrimidine-sulfonanilide herbicide) (5 to 150 g AS/ha, especially 10-20 g AS/ha), (C2.14) fluthiacet and salts and esters thereof such as fluthiacet-methyl (KIH-9201; PM, p. 606-608) (1-50 g AS/ha, especially 2-40 g AS/ha) and/or (C2.15) oxasulfuron (PM, p. 911-912) (10-300 g AS/ha, especially 20-200 g AS/ha) and/or (C3) herbicides with selective action in soybeans against monocotyledonous weeds and having foliar and soil action, for example cyclohexanediones from the group of (C3.1) sethoxydim (PM, p. 1101-1103) (50 to 3000 g AS/ha, especially 100 to 2000 g AS/ha), (C3.2) cycloxydim (PM, p. 290-291) (10 to 1000 g AS/ha, especially 30 to 800 g AS/ha) and (C3.3) clethodim (PM, p. 250-251) (10 to 800 g AS/ha, especially 20 to 600 g AS/ha) and/or (C4) herbicides with selective action in soybeans against monocotyledonous weeds and having foliar action, for example (het)aryloxyphenoxy herbicides such as (C4.1) quizalofop-P and esters thereof such as the ethyl or tefuryl ester (PM, p. 1089-1092), also in the form of mixtures with the other optical isomer, for example racemic quizalofop and esters thereof (10-300 g AS/ha, especially 20-250 g AS/ha), (C4.2) fenoxaprop-P and esters thereof such as the ethyl ester (PM, p. 519-520) (10 to 300 g AS/ha, especially 20 to 250 g AS/ha), also in the form of mixtures with the other optical isomer, for example as racemic fenoxaprop-ethyl, (C4.3) fluazifop-P and esters thereof such as the butyl ester (PM, p. 556-557) (20 to 1500 g AS/ha, especially 30 to 1200 g AS/ha), also in the form of mixtures with the other optical isomer, for example as racemic fluazifop-butyl, (C4.4) haloxyfop and haloxyfop-P and esters thereof such as the methyl or etotyl ester (PM, p. 660-663) (10-300 g AS/ha, especially 20 to 250 g AS/ha) and/or (C4.5) propaquizafop (PM, p. 1021-1022) (10-300 g AS/ha, especially 20-250 g AS/ha) and/or (C5) nonselective herbicides usable for specific purposes in soybeans, for example (C5.1) paraquat (salts) such as paraquat dichloride (PM, p. 923-925) (250 to 5000 g AS/ha, especially 500 to 4000 g AS/ha).

TABLE 2

| No. | Active ingredient (A) | Active ingredient (B) | Active ingredient (C) |
| --- | --- | --- | --- |
| 1 | A1.1 | B1.0 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 2 | A1.1 | B1.0 | C1.1, C1.2, C1.3, C1.4, C1.5, C1.6, C1.7, C1.8, C1.9, |

TABLE 2-continued

| No. | Active ingredient (A) | Active ingredient (B) | Active ingredient (C) |
|---|---|---|---|
| | | | C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 3 | A1.1 | B1.0 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 4 | A1.1 | B1.0 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 5 | A1.1 | B1.1 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 6 | A1.1 | B1.1 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 7 | A1.1 | B1.1 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 8 | A1.1 | B1.1 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 9 | A1.1 | B1.2 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 10 | A1.1 | B1.2 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 11 | A1.1 | B1.2 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 12 | A1.1 | B1.2 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 13 | A1.1 | B1.3 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 14 | A1.1 | B1.3 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 15 | A1.1 | B1.3 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 16 | A1.1 | B1.3 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 17 | A1.1 | B1.4 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 18 | A1.1 | B1.4 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 19 | A1.1 | B1.4 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 20 | A1.1 | B1.4 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 21 | A1.1 | B1.5 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 22 | A1.1 | B1.5 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 23 | A1.1 | B1.5 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 24 | A1.1 | B1.5 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 25 | A1.1 | B1.6 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 26 | A1.1 | B1.6 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 27 | A1.1 | B1.6 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 28 | A1.1 | B1.6 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 29 | A1.1 | B1.7 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 30 | A1.1 | B1.7 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 31 | A1.1 | B1.7 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 32 | A1.1 | B1.7 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 33 | A1.1 | B1.8 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 34 | A1.1 | B1.8 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 35 | A1.1 | B1.8 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 36 | A1.1 | B1.8 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 37 | A1.1 | B1.9 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 38 | A1.1 | B1.9 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 39 | A1.1 | B1.9 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 40 | A1.1 | B1.9 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 41 | A1.1 | B1.10 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 42 | A1.1 | B1.10 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 43 | A1.1 | B1.10 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 44 | A1.1 | B1.10 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 45 | A1.1 | B1.11 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 46 | A1.1 | B1.11 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 47 | A1.1 | B1.11 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 48 | A1.1 | B1.11 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 49 | A1.1 | B1.12 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 50 | A1.1 | B1.12 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 51 | A1.1 | B1.12 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 52 | A1.1 | B1.12 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 53 | A1.1 | B1.13 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 54 | A1.1 | B1.13 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 55 | A1.1 | B1.13 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 56 | A1.1 | B1.13 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 57 | A1.1 | B1.14 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 58 | A1.1 | B1.14 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 59 | A1.1 | B1.14 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 60 | A1.1 | B1.14 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 61 | A1.1 | B1.15 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 62 | A1.1 | B1.15 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 63 | A1.1 | B1.15 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 64 | A1.1 | B1.15 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 65 | A1.1 | B1.16 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 66 | A1.1 | B1.16 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 67 | A1.1 | B1.16 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 68 | A1.1 | B1.16 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 69 | A1.1 | B1.17 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 70 | A1.1 | B1.17 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 71 | A1.1 | B1.17 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 72 | A1.1 | B1.17 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
|  |  |  | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 73 | A1.1 | B1.18 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 74 | A1.1 | B1.18 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 75 | A1.1 | B1.18 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 76 | A1.1 | B1.18 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 77 | A1.1 | B1.19 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 78 | A1.1 | B1.19 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 79 | A1.1 | B1.19 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 80 | A1.1 | B1.19 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 81 | A1.1 | B1.20 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 82 | A1.1 | B1.20 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 83 | A1.1 | B1.20 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 84 | A1.1 | B1.20 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 85 | A1.1 | B1.21 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 86 | A1.1 | B1.21 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 87 | A1.1 | B1.21 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 88 | A1.1 | B1.21 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 89 | A1.1 | B1.22 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 90 | A1.1 | B1.22 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 91 | A1.1 | B1.22 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 92 | A1.1 | B1.22 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 93 | A1.1 | B1.23 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 94 | A1.1 | B1.23 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 95 | A1.1 | B1.23 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 96 | A1.1 | B1.23 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 97 | A1.2 | B1.0 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 98 | A1.2 | B1.0 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 99 | A1.2 | B1.0 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 100 | A1.2 | B1.0 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 101 | A1.2 | B1.1 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 102 | A1.2 | B1.1 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 103 | A1.2 | B1.1 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 104 | A1.2 | B1.1 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 105 | A1.2 | B1.2 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 106 | A1.2 | B1.2 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 107 | A1.2 | B1.2 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 108 | A1.2 | B1.2 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 109 | A1.2 | B1.3 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 110 | A1.2 | B1.3 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 111 | A1.2 | B1.3 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 112 | A1.2 | B1.3 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 113 | A1.2 | B1.4 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 114 | A1.2 | B1.4 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 115 | A1.2 | B1.4 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 116 | A1.2 | B1.4 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 117 | A1.2 | B1.5 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 118 | A1.2 | B1.5 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 119 | A1.2 | B1.5 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 120 | A1.2 | B1.5 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 121 | A1.2 | B1.6 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient C |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 122 | A1.2 | B1.6 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 123 | A1.2 | B1.6 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 124 | A1.2 | B1.6 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 125 | A1.2 | B1.7 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 126 | A1.2 | B1.7 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 127 | A1.2 | B1.7 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 128 | A1.2 | B1.7 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 129 | A1.2 | B1.8 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 130 | A1.2 | B1.8 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 131 | A1.2 | B1.8 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 132 | A1.2 | B1.8 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 133 | A1.2 | B1.9 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 134 | A1.2 | B1.9 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 135 | A1.2 | B1.9 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 136 | A1.2 | B1.9 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 137 | A1.2 | B1.10 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 138 | A1.2 | B1.10 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 139 | A1.2 | B1.10 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 140 | A1.2 | B1.10 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 141 | A1.2 | B1.11 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 142 | A1.2 | B1.11 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 143 | A1.2 | B1.11 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 144 | A1.2 | B1.11 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 145 | A1.2 | B1.12 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 146 | A1.2 | B1.12 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 147 | A1.2 | B1.12 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 148 | A1.2 | B1.12 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 149 | A1.2 | B1.13 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 150 | A1.2 | B1.13 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 151 | A1.2 | B1.13 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 152 | A1.2 | B1.13 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 153 | A1.2 | B1.14 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 154 | A1.2 | B1.14 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 155 | A1.2 | B1.14 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 156 | A1.2 | B1.14 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 157 | A1.2 | B1.15 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 158 | A1.2 | B1.15 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 159 | A1.2 | B1.15 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 160 | A1.2 | B1.15 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 161 | A1.2 | B1.16 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 162 | A1.2 | B1.16 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 163 | A1.2 | B1.16 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 164 | A1.2 | B1.16 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 165 | A1.2 | B1.17 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 166 | A1.2 | B1.17 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 167 | A1.2 | B1.17 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 168 | A1.2 | B1.17 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 169 | A1.2 | B1.18 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 170 | A1.2 | B1.18 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 171 | A1.2 | B1.18 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 172 | A1.2 | B1.18 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 173 | A1.2 | B1.19 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 174 | A1.2 | B1.19 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 175 | A1.2 | B1.19 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 176 | A1.2 | B1.19 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 177 | A1.2 | B1.20 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 178 | A1.2 | B1.20 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 179 | A1.2 | B1.20 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 180 | A1.2 | B1.20 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 181 | A1.2 | B1.21 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 182 | A1.2 | B1.21 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 183 | A1.2 | B1.21 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 184 | A1.2 | B1.21 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient C |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 185 | A1.2 | B1.22 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 186 | A1.2 | B1.22 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 187 | A1.2 | B1.22 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 188 | A1.2 | B1.22 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 189 | A1.2 | B1.23 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 190 | A1.2 | B1.23 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 191 | A1.2 | B1.23 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 192 | A1.2 | B1.23 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 193 | A1.3 | B1.0 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 194 | A1.3 | B1.0 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 195 | A1.3 | B1.0 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 196 | A1.3 | B1.0 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 197 | A1.3 | B1.1 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 198 | A1.3 | B1.1 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 199 | A1.3 | B1.1 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 200 | A1.3 | B1.1 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 201 | A1.3 | B1.2 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 202 | A1.3 | B1.2 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 203 | A1.3 | B1.2 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 204 | A1.3 | B1.2 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 205 | A1.3 | B1.3 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 206 | A1.3 | B1.3 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 207 | A1.3 | B1.3 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 208 | A1.3 | B1.3 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 209 | A1.3 | B1.4 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 210 | A1.3 | B1.4 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 211 | A1.3 | B1.4 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 212 | A1.3 | B1.4 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 213 | A1.3 | B1.5 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 214 | A1.3 | B1.5 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 215 | A1.3 | B1.5 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 216 | A1.3 | B1.5 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 217 | A1.3 | B1.6 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 218 | A1.3 | B1.6 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 219 | A1.3 | B1.6 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 220 | A1.3 | B1.6 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 221 | A1.3 | B1.7 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 222 | A1.3 | B1.7 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 223 | A1.3 | B1.7 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 224 | A1.3 | B1.7 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 225 | A1.3 | B1.8 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 226 | A1.3 | B1.8 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 227 | A1.3 | B1.8 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 228 | A1.3 | B1.8 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 229 | A1.3 | B1.9 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 230 | A1.3 | B1.9 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 231 | A1.3 | B1.9 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 232 | A1.3 | B1.9 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 233 | A1.3 | B1.10 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 234 | A1.3 | B1.10 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 235 | A1.3 | B1.10 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 236 | A1.3 | B1.10 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 237 | A1.3 | B1.11 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 238 | A1.3 | B1.11 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 239 | A1.3 | B1.11 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 240 | A1.3 | B1.11 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 241 | A1.3 | B1.12 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 242 | A1.3 | B1.12 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 243 | A1.3 | B1.12 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 244 | A1.3 | B1.12 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 245 | A1.3 | B1.13 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 246 | A1.3 | B1.13 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 247 | A1.3 | B1.13 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 248 | A1.3 | B1.13 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 249 | A1.3 | B1.14 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 250 | A1.3 | B1.14 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 251 | A1.3 | B1.14 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 252 | A1.3 | B1.14 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 253 | A1.3 | B1.15 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 254 | A1.3 | B1.15 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 255 | A1.3 | B1.15 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 256 | A1.3 | B1.15 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 257 | A1.3 | B1.16 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 258 | A1.3 | B1.16 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 259 | A1.3 | B1.16 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 260 | A1.3 | B1.16 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 261 | A1.3 | B1.17 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 262 | A1.3 | B1.17 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 263 | A1.3 | B1.17 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 264 | A1.3 | B1.17 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 265 | A1.3 | B1.18 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 266 | A1.3 | B1.18 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 267 | A1.3 | B1.18 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 268 | A1.3 | B1.18 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 269 | A1.3 | B1.19 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 270 | A1.3 | B1.19 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 271 | A1.3 | B1.19 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 272 | A1.3 | B1.19 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 273 | A1.3 | B1.20 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 274 | A1.3 | B1.20 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 275 | A1.3 | B1.20 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 276 | A1.3 | B1.20 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 277 | A1.3 | B1.21 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 278 | A1.3 | B1.21 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 279 | A1.3 | B1.21 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 280 | A1.3 | B1.21 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 281 | A1.3 | B1.22 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 282 | A1.3 | B1.22 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, |

TABLE 2-continued

| No. | Active ingredient (A) | Active ingredient (B) | Active ingredient (C) |
|---|---|---|---|
| | | | C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 283 | A1.3 | B1.22 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 284 | A1.3 | B1.22 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 285 | A1.3 | B1.23 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 286 | A1.3 | B1.23 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 287 | A1.3 | B1.23 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |
| 288 | A1.3 | B1.23 | C1.1, C1.2, C1.3, C1.4, C1.5, C1.6, C1.7, C1.8, C1.9, C1.10, C1.11, C1.12, C1.13, C1.14, C1.15, C1.16, C1.17, C1.18, C1.19, C1.20; C1.21, C1.22, C1.23, C1.24, C1.25, C1.26, C1.27, C1.28, C1.29, C1.30; C2.1, C2.2, C2.3, C2.4, C2.5, C2.6, C2.7, C2.8, C2.9, C2.10, C2.11, C2.12, C2.13, C2.14, C2.15; C3.1, C3.2, C3.3; C4.1, C4.2, C4.3, C4.4, C4.5; C5.1 |

The application rates of the active ingredients (C) may vary significantly. The following ranges may be a rough guide:

Generally 0.5-5000 g AS/ha, preferably 1 to 4000 g AS/ha, more preferably 1.5-3000 g AS/ha.

Some of the combinations mentioned are novel and as such also form part of the subject matter of the invention.

The inventive combinations (=herbicidal compositions) have excellent herbicidal efficacy against a broad spectrum of economically important mono- and dicotyledonous weeds. The active ingredients also give good coverage of perennial weeds which produce shoots from rhizomes, rootstocks or other permanent organs and are difficult to control. It is unimportant whether the substances are deployed prior to sowing, pre-emergence or post-emergence. Preference is given to post-emergence application, or early post-sowing pre-emergence application.

Specific examples are given of some representatives of the mono- and dicotyledonous weed flora which can be controlled by the inventive compositions, without any intention of restriction to particular species through the enumeration.

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

The invention also includes control of those weeds from both groups which are resistant to one or more herbicides or herbicide groups, for example those weeds which, due to target site resistance or metabolic resistance, can no longer be controlled by ACCAse inhibitors, ALS inhibitors or EPSPS inhibitors, and also auxins; HPPD inhibitors.

When the inventive compositions are applied to the surface of the earth prior to germination, either the emergence of the weed seedlings is completely prevented or the weeds grow as far as the cotyledon stage but then stop growing and finally die completely after three to four weeks.

In the case of application of the compositions to the green plant parts post-emergence, there is likewise a very rapid and severe cessation of growth after the treatment, and the weed plants remain at the growth stage present at the application time or die completely after a certain time, such that weed competition, which is harmful to crop plants, is thus eliminated in a very early and sustainable manner.

The inventive herbicidal compositions are notable, compared to the individual preparations, for a faster onset and longer duration of herbicidal action. The rain resistance of the active ingredients in the inventive combinations is generally favorable. A particular advantage which has to be considered is the fact that the dosages of compounds (A) and (B) which are used and are effective in the combinations can be set at a sufficiently low level that the soil action thereof is optimal and advantageous with respect to subsequent crops. Thus, the use thereof does not just become possible in sensitive crops, but groundwater contaminations are virtually avoided. The inventive combination of active ingredients enables a considerable reduction in the necessary application rate of the active ingredients.

In the case of combined application of herbicides of the (A)+(B) type, superadditive (=synergistic) effects occur. In this case, the action in the combinations is greater than the expected sum of effects of the individual herbicides used. The synergistic effects allow a reduction in the application rate, the control of a broader spectrum of broad-leaved weeds and weed grasses (more particularly also of resistant broad-leaved weeds and weed grasses), faster onset of the herbicidal action, longer duration of action, better control of the weeds with only one application or few applications, and a widening of the possible application period. In some cases, the use of the compositions also reduces the amount of harmful constituents in the crop plant, such as nitrogen or oleic acid.

The properties and advantages mentioned are required in practical weed control in order to keep agricultural crops free of unwanted competing plants, and thus to qualitatively and quantitatively ensure and/or increase the yields. The technical standard is far exceeded by these novel combinations with regard to the properties described.

Even though the inventive compositions have excellent herbicidal activity against mono- and dicotyledonous weeds, the tolerant or cross-tolerant soybean plants are damaged only insignificantly, if at all.

Furthermore, some of the inventive compositions have excellent growth-regulating properties in the soybean and leguminous species. They intervene to regulate the plant's own metabolism and can thus be used for controlled influence of plant constituents. In addition, they are also suitable for general control and inhibition of unwanted vegetative growth without damaging the plants. Inhibition of vegetative growth is very important in the case of many mono- and dicotyledonous crops, since lodging can be reduced or completely prevented by improved stability.

Due to their herbicidal and plant growth regulation properties, the compositions can be used to control weeds in known tolerant or cross-tolerant soybean and leguminous species, or tolerant or genetically modified soybean and leguminous species yet to be developed. The transgenic plants are generally notable for particularly advantageous properties, as well as resistances to the inventive compositions, for example for resistances to plant diseases or pathogens of plant diseases, such as particular insects or microorganisms such as fungi, bacteria or viruses. Other particular properties relate, for example, to the harvested material in respect of amount, quality, storability, composition of specific constituents. For instance, there are known transgenic plants with elevated protein content of desired ingredients or modified quality, for example different fatty acid and/or amino acid composition of the harvested material.

Conventional ways of producing novel plants which have modified properties in comparison to plants which have occurred to date consist, for example, in traditional breeding methods and the generation of mutants. Alternatively, novel plants with modified properties can be generated with the aid of recombinant methods (see, for example, EP-A 0 221 044, EP-A 0 131 624). For example, there have been many descriptions of:

recombinant modifications of crop plants for the purpose of modifying the starch synthesized in the plants (e.g. WO 92/011376 A, WO 92/014827 A, WO 91/019806 A), transgenic crop plants which are resistant to particular herbicides of the glyphosate type (WO 92/000377 A) or sulfonylurea type (EP 0 257 993 A, U.S. Pat. No. 5,013,659) or to combinations or mixtures of these herbicides as a result of "gene stacking", such as transgenic crop plants, for example corn or soybean with the trade name or the designation Optimum™ GAT™ (Glyphosate ALS Tolerant), transgenic crop plants, for example cotton, with the ability to produce *Bacillus thuringiensis* toxins (Bt toxins) which make the plants resistant to particular pests (EP-A 0 142 924, EP-A 0 193 259), transgenic crop plants with a modified fatty acid composition (WO 91/013972 A), genetically modified crop plants with novel constituents or secondary metabolites, for example novel phytoalexins, which cause an increased disease resistance (EP 0 309 862 A, EP 0 464 461 A), genetically modified plants with reduced photorespiration, which have higher yields and higher stress tolerance (EP 0 305 398 A), transgenic crop plants which produce pharmaceutically or diagnostically important proteins ("molecular pharming"), transgenic crop plants which are notable for higher yields or better quality, transgenic crop plants which are notable for a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

For such recombinant manipulations, nucleic acid molecules which allow mutagenesis or a sequence change by recombination of DNA sequences can be introduced into plasmids. With the aid of standard methods, it is possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

The production of plant cells with a reduced activity of a gene product can be achieved, for example, by the expression of at least one appropriate antisense RNA, or of a sense RNA for achievement of a cosuppression effect, or the expression of at least one appropriately constructed ribozyme which specifically cleaves transcripts of the abovementioned gene product.

For this purpose, it is firstly possible to use DNA molecules which comprise the entire coding sequence of a gene product including any flanking sequences present, or else DNA molecules which comprise only parts of the coding sequence, in which case these parts must be long enough to bring about an antisense effect in the cells. It is also possible to use DNA sequences which have a high degree of homology to the coding sequences of a gene product, but are not completely identical.

When expressing nucleic acid molecules in plants, the protein synthesized may be localized in any desired compartment of the plant cell. However, in order to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give complete plants. In principle, the transgenic plants may be plants of any desired plant species, i.e. both monocotyledonous and dicotyledonous plants.

Thus, it is possible to obtain transgenic plants whose properties are altered by overexpression, suppression or inhibition of homologous (=natural) genes or gene sequences, or expression of heterologous (=foreign) genes or gene sequences.

The inventive compositions can be used with preference in transgenic soybean and leguminous species which are resistant not only to component (A) but also to growth regulators (for example 2,4-D or dicamba), to compounds of group (B) or to herbicides which inhibit essential plant enzymes, for example acetolactate synthases (ALS), EPSP synthases or hydroxyphenylpyruvate dioxygenases (HPPD), or to herbicides from the group of the sulfonylureas, the glyphosates or benzoylisoxazoles and analogous active ingredients, or to any desired combinations of these active ingredients.

The inventive compositions can be used with particular preference in transgenic soybean and leguminous species which are tolerant to a combination of glyphosates and glufosinates or to a combination of glufosinates and sulfonylureas or imidazolinones and/or HPPD inhibitors.

The invention therefore also provides a process for control of unwanted plant growth in tolerant soybean and leguminous species, which comprises applying one or more herbicides of type (A) with one or more herbicides of type (B) to the weeds, plant parts thereof or the cultivated area.

The invention also provides the novel combinations of compounds (A)+(B) and herbicidal compositions comprising them.

The inventive active ingredient combinations may be present either in the form of co-formulations or blend formulations of the two components, optionally with further active ingredients, additives and/or customary formulation assistants, which are then employed diluted with water in a customary manner, or as what are called tankmixes by combined dilution of the separately formulated or partially separately formulated components with water.

The inventive compositions can be used in the form of wettable powders, emulsifiable concentrates, sprayable solutions, dusting products or granules in the customary formulations. The invention therefore also provides herbicidal and plant growth-regulating compositions which comprise the inventive compositions.

The inventive compositions can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-Active Ethylene Oxide Adducts], Wiss. Verlagsgesell, Stuttgart 1976; Winnacker-Küchler, "Chemische Technologie", Volume 7, C. Hanser Verlag Munich, 4th Ed. 1986.

Based on these formulations, it is also possible to prepare combinations with other pesticidally active ingredients, such as, for example, insecticides, acaricides, herbicides, fungicides, and also with safeners, fertilizers and/or growth regulators, for example in the form of a finished formulation or as a tankmix.

Wettable powders are preparations which can be dispersed uniformly in water and, as well as the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleylmethyltauride. To prepare the wettable powders, the active herbicidal ingredients are ground finely, for example in customary apparatus such as hammer mills, blower mills and air-jet mills and simultaneously or subsequently mixed with the formulation assistants.

Emulsifiable concentrates are prepared by dissolving the active ingredient in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active ingredient onto adsorptive granulated inert material or by applying active ingredient concentrates by means of adhesives, for example polyvinyl alcohol, sodium polyacrylate or else mineral oils, onto the surface of carriers such as sand, kaolinites or of granulated inert material. It is also possible to granulate suitable active ingredients in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of inventive compositions.

In wettable powders, the active ingredient concentration is, for example, from about 10 to 90% by weight; the remainder to 100% by weight consists of customary formulation constituents. In the case of emulsifiable concentrates, the active ingredient concentration may be from about 1 to 90% by weight, preferably from 5 to 80% by weight. Dust-type formulations contain from 1 to 30% by weight of active ingredient, preferably usually from 5 to 20% by weight of active ingredient; sprayable solutions contain from about 0.05 to 80% by weight, preferably from 2 to 50% by weight of active ingredient. In water-dispersible granules, the active ingredient content depends partly on whether the active compound is present in solid or liquid form and which granulation assistants, fillers, etc. are used. In the granules dispersible in water, the content of active ingredient is, for example, between 1 and 95% by weight, preferably between 10 and 80% by weight.

In addition, the active ingredient formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

For example, it is known that the action of glufosinate-ammonium (A1.2), and likewise that of the L-enantiomer thereof, can be improved by surface-active substances, preferably by wetting agents from the group of the alkyl polyglycol ether sulfates which contain, for example, 6 to 18 carbon atoms and are used in the form of their alkali metal or ammonium salts, but also as the magnesium salt, such as C12/C14 fatty alcohol diglycol ether sulfate sodium (®Genapol LRO, Hoechst); see EP-A-0 476 555, EP-A-0 048 436, EP-A-0 336 151 or U.S. Pat. No. 4,400,196 and Proc. EWRS Symp. "Factors Affecting Herbicidal Activity and Selectivity", 227-232 (1988). It is additionally known that alkyl polyglycol ether sulfates are also suitable as penetration aids and action enhancers for a number of other herbicides, including herbicides from the group of the imidazolinones; see EP-A-0 502 014.

For use, the formulations present in commercial standard form are optionally diluted in a customary manner, for example by means of water in the case of wettable powders, emulsifiable concentrates, dispersions and water-dispersible granules. Dust formulations, soil granules and scattering granules, and sprayable solutions are not normally diluted with further inert substances before use.

The active ingredients can be deployed on the plants, plant parts, plant seeds or the cultivated area (agricultural or horticultural useful area), preferably on the green plants and plant parts, and optionally additionally on the soil.

One means of application is the combined deployment of the active ingredients in the form of tankmixes, in which case the optionally formulated concentrated formulations of the individual active ingredients are mixed together in the tank with water and/or fertilizer solutions, and the resulting spray liquor is deployed.

A combined herbicidal formulation of the inventive combination of active ingredients (A) and (B) has the advantage of easier applicability because the amounts of the components have already been set in the right ratio relative to one another. In addition, the assistants in the formulation can be optimally adjusted to one another, while a tankmix of different formulations can give rise to unwanted combinations of active ingredients.

A. Formulation Examples a) A dusting product is obtained by mixing 10 parts by weight of a compound of an inventive active ingredient combination and 90 parts by weight of talc as an inert substance, and comminuting the mixture in a hammer mill.

b) A readily water-dispersible wettable powder is obtained by mixing 25 parts by weight of an inventive active ingredient combination, 64 parts by weight of kaolin-containing quartz as an inert substance, 10 parts by weight of potassium lignosulfonate and 1 part by weight of sodium oleylmethyltaurate as a wetting agent and dispersant, and grinding the mixture in a pinned-disk mill.

c) A readily water-dispersible dispersion concentrate is obtained by mixing 20 parts by weight of an inventive active ingredient combination with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a ball mill to a fineness of below 5 microns.

d) An emulsifiable concentrate is obtained from 15 parts by weight of an inventive active ingredient combination, 75 parts by weight of cyclohexanone as a solvent and 10 parts by weight of ethoxylated nonylphenol as an emulsifier.

e) Water-dispersible granules are obtained by mixing
75 parts by weight of an inventive active ingredient combination,
10 parts by weight of calcium lignosulfonate,
5 parts by weight of sodium laurylsulfate,
3 parts by weight of polyvinyl alcohol and
7 parts by weight of kaolin,
grinding the mixture in a pinned-disk mill and granulating the powder in a fluidized bed by spraying on water as a granulating liquid.

f) Water-dispersible granules are also obtained by homogenizing and precomminuting
25 parts by weight of an inventive active ingredient combination,
5 parts by weight of sodium 2,2'-dinaphthylmethane-6,6'-disulfonate,
2 parts by weight of sodium oleylmethyltaurate,
1 part by weight of polyvinyl alcohol,
17 parts by weight of calcium carbonate and
50 parts by weight of water
in a colloid mill, then grinding the mixture in a bead mill and atomizing and drying the resulting suspension in a spray tower by means of a one-substance nozzle.

B. Biological Examples

1. Pre-Emergence Herbicidal Action

Seeds or rhizome pieces of mono- and dicotyledonous weeds are placed in sandy lome in plastic or cardboard pots and covered with soil. The compositions formulated in the form of concentrated aqueous solutions, wettable powders or emulsion concentrates are then applied to the surface of the covering soil as an aqueous solution, suspension or emulsion in different dosages with a water application rate of 100 to 800 l/ha (equivalent). After the treatment, the pots are placed in a greenhouse and kept under good growth conditions for the weeds. The plant or emergence damage was scored visually after the emergence of the test plants after a test period of 3 to 8 weeks, compared to untreated controls. As the test results show, the inventive compositions have good herbicidal pre-emergence efficacy against a wide spectrum of weed grasses and broad-leaved weeds.

Frequently, effects of the inventive combinations exceeding the formal sum of the effects on individual application of the herbicides are observed (=synergistic action).

When the action values observed (=E) already exceed the formal sum (EA=A+B) of the values for the experiments with individual active ingredients, they then likewise exceed the expected value according to Colby (=EC), which is calculated by the following formula and the exceedance of which is likewise considered to be an (indication of) synergism (cf. S. R. Colby; in Weeds 15 (1967) p. 20 to 22):

$$EC = A + B - (A \cdot B/100)$$

In this formula: A, B=Action of active ingredients A and B in % for, respectively, a and b g AS/ha; EC=Expected value in % for a+b g AS/ha.

The observed values of the experiments show, at suitable low dosages, an effect of the combinations above the expected values according to Colby.

2. Post-Emergence Herbicidal Action

Seeds or rhizome pieces of mono- and dicotyledonous weeds are placed in sandy lome in cardboard pots, covered with soil and grown in a greenhouse under good growth conditions. Three weeks after sowing, the test plants are treated with the inventive compositions at the three-leaf stage. The inventive compositions formulated as wettable powders or as emulsion concentrates are sprayed onto the green plant parts at different dosages with a water application rate of 600 to 800 l/ha (equivalent). After the test plants have been left to stand in the greenhouse under optimal growth conditions for about 3 to 4 weeks, the effect of the preparations is scored visually compared to untreated controls. The inventive compositions also have good post-emergence herbicidal efficacy against a broad spectrum of economically important weed grasses and broad-leaved weeds.

Frequently, effects of the inventive combinations which exceed the formal sum of the effects on individual application of the herbicides are observed. The observed values in the experiments show, at suitable low dosages, an effect of the combinations which is above the expected values according to Colby (cf. scoring in example 1).

3. Herbicidal Action and Crop Plant Compatibility (Field Trial)

Plants of transgenic soybean and leguminous species having resistance to one or more herbicides (A) are grown together with typical weed plants in the open on plots of 2×5 m in size under natural outdoor conditions; as an alternative, weed growth sets in naturally as the soybean plants are grown. The treatment with the inventive compositions and, for control, separately with sole application of the component active ingredients is effected under standard conditions with a plot spraying system at a water application rate of 100-400 liters of water per hectare in parallel trials according to the scheme from table 3, i.e. pre-sowing, post-sowing pre-emergence, or post-emergence at the early, middle or late stage.

TABLE 3

Application scheme - Examples[1]

| Application of active ingredients | Pre-sowing | Pre-emergence after sowing | Post-emergence 1-2 leaves | Post-emergence 2-4 leaves | Post-emergence 6 leaves |
|---|---|---|---|---|---|
| combined | (A) + (B) | | | | |
| " | | (A) + (B) | | | |
| " | | | (A) + (B) | | |
| " | | | | (A) + (B) | |
| " | | | | | (A) + (B) |
| sequential | (A) | | (B) | | |
| " | | (A) | (B) | | |
| " | | (A) | | (B) | |
| " | | (A) | (A) | (B) | |
| " | | (A) | | (B) | (B) |
| " | | (A) | | (A) + (B) | |
| " | (B) | | (A) | | |
| " | | (B) | | (A) + (B) | |
| " | (A) + (B) | | (A) + (B) | | |
| " | (A) + (B) | (A) + (B) | (A) + (B) | | |
| " | | (A) + (B) | (A) + (B) | | |
| " | | (A) + (B) | (A) + (B) | (A) + (B) | |
| " | | (A) + (B) | (A) + (B) | (A) + (B) | (A) + (B) |
| " | | | (A) + (B) | (A) + (B) | |
| " | | | (A) + (B) | (A) + (B) | (A) + (B) |
| " | | | | (A) + (B) | (A) + (B) |

[1]In each case, a C component can be mixed into A)/B) or A + B), or can be applied in sequence before or after the application of A)/B) or A + B).

2 to 8 weeks after application, the herbicidal efficacy of the active ingredients or active ingredient mixtures is scored visually by comparing the treated plots to untreated control plots. This covers damage and development of all above-ground plant parts. The scoring is effected according to a percent scale (100% effect=all plants dead; 50% effect=50% of the plants and green plant parts dead; 0% effect=no discernible effect=like control plot). The scoring values of 2-4 plots in each case is averaged.

The comparison showed that the inventive combinations usually have more, in some cases considerably more, herbicidal effect than the sum of the effects of the individual herbicides. The effects were above the expected values according to Colby within significant parts of the scoring period and demonstrate synergism. The soybean and leguminous species, in contrast, were damaged only insignificantly, if at all, as a result of the treatments with the herbicidal compositions.

Abbreviations used generally in the tables:

g AS/ha=grams of active substance (100% active ingredient) per hectare $E^A$=sum of the herbicidal effects of the individual applications (expected value by the addition method)

$E^C$=expected value according to Colby (cf. scoring for table 1)

"Soja LL"=®Liberty-Link soya, tolerant or resistant to glufosinate-ammonium

The invention claimed is:

1. A herbicide combination capable of being used for control of weeds in soybean and/or leguminous species, said herbicide combination comprising:

(A) a herbicide selected from the group consisting of compounds of formula (A1)

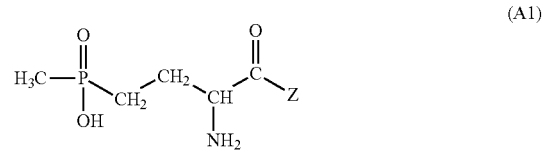

in which Z is hydroxyl, —NHCH(CH$_3$)CONHCH(CH$_3$)COOH or —NHCH(CH$_3$)CONHCH[CH$_2$CH(CH$_3$)$_2$]COOH, and/or esters and/or salts thereof, (B) a herbicide of formula (B1)

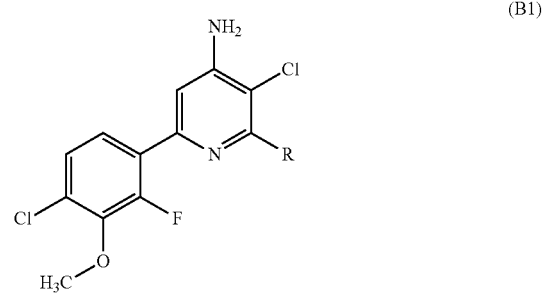

in which R is CO$_2$H and/or a herbicide-active derivative, (C) a herbicide selected from the group consisting of trifluralin (C1.1), metribuzin (C1.2), clomazone (C1.3), pendimethalin (C1.4), metolachlor/S-metolachlor (C1.5), flumetsulam (C1.6), dimethenamid/dimethenamid-p (C1.7), alachlor (C1.8), sulfentrazone (C1.10), ethalfluralin (C1.11), norflurazon (C1.13), flumioxazin (C1.15), imazapyr/imazapyr-isopropylammonium (C1.16), imazamox/imazamox-ammonium (C1.17), imazaquin/imazaquin-ammonium (C1.18), carfentrazone (C.1.20), imazethapyr/imazethapyr-ammonium (C.1.21), dicamba (C.1.22), mesotrione (C.1.23), pyrasulfutole (C.1.26), tembotrione (C.1.27), isoxaflutole (C.1.28), sulcotrione (C.1.29), bentazone (C2.2), thifensulfuron (C2.3), oxyfluorfen (C2.4), lactofen (C2.5), fomesafen (C2.6), flumiclorac (C2.7), acifluorfen and the sodium salt thereof (C2.8), 2,4-DB (C2.9), 2,4-D (C2.10) chlorimuron/chlorimuron-ethyl (C2.11), cloransulam/cloransulam-methyl (C2.12), diclosulam (2.13), oxasulfuron (C2.15), sethoxydim (C3.1), cycloxydim (C3.2), clethodim (C3.3), quizalofop-P and the ethyl or tefuryl ester thereof (C4.1), fenoxaprop-P and the ethyl ester thereof (C4.2), fluazifop-P and the butyl ester thereof (C4.3), haloxyfop/haloxyfop-P and the methyl or ethyl ester thereof (C4.4), propaquizafop (C4.5), and paraquat/paraquat dichloride (C5.1), wherein said combination exhibits herbicide efficacy greater than expected for combinations of component (C) with mixture of components (A) and (B)

and wherein the soybean species is tolerant to the herbicides (A), (B), and (C) present in the combination.

2. The herbicide combination as claimed in claim 1, wherein said herbicide combination comprises at least one further active ingredient selected from the group consisting of safeners, plant growth regulators, herbicides, fungicides and/or insecticides.

3. The herbicide combination as claimed in claim 1, wherein said soybean species is tolerant to said herbicide combination in the presence of a safener.

4. The herbicide combination as claimed in claim 1, wherein said component (C) is selected from the group consisting of clethodim, cycloxydim and fenoxaprop-P-ethyl.

5. The herbicide combination as claimed in claim 1, wherein glufosinate-ammonium is present as component (A).

6. The herbicide combination as claimed in claim 1, wherein said soybean species is additionally tolerant to 2,4-D, dicamba, imidazolinone, and/or to herbicides which inhibit acetolactate synthase (ALS), EPSP synthase and/or hydroxyphenylpyruvate dioxygenase (HPPD).

7. The herbicide combination as claimed in claim 6, wherein said soybean species is tolerant to 2,4-D, dicamba, at least one sulfonylurea herbicide, at least one sulfonamide herbicide, glyphosate, mesotrione, bicyclopyrone, pyrasulfutole, tembotrione, sulcotrione, topramezone and/or isoxaflutole.

8. The herbicide combination as claimed in claim 1, wherein component (B) is selected from
4-amino-3-chloro-6-(4-chloro-2-fluoro-3-methoxyphenyl)pyridine-2-carboxylic acid (B1.0),
methyl 4-amino-3-chloro-6-(4-chloro-2-fluoro-3-methoxyphenyl)pyridine-2-carboxylate (B1.1),
ethyl 4-amino-3-chloro-6-(4-chloro-2-fluoro-3-methoxyphenyl)pyridine-2-carboxylate (B1.2),
n-propyl 4-amino-3-chloro-6-(4-chloro-2-fluoro-3-methoxyphenyl)pyridine-2-carboxylate (B1.3),
i-propyl 4-amino-3-chloro-6-(4-chloro-2-fluoro-3-methoxyphenyl)pyridine-2-carboxylate (B1.4),
n-butyl 4-amino-3-chloro-6-(4-chloro-2-fluoro-3-methoxyphenyl)pyridine-2-carboxylate (B1.5),
2-butyl 4-amino-3-chloro-6-(4-chloro-2-fluoro-3-methoxyphenyl)pyridine-2-carboxylate (B1.6),
tert-butyl 4-amino-3-chloro-6-(4-chloro-2-fluoro-3-methoxyphenyl)pyridine-2-carboxylate (B1.7),
allyl 4-amino-3-chloro-6-(4-chloro-2-fluoro-3-methoxyphenyl)pyridine-2-carboxylate (B1.8),
2-butoxyethyl 4-amino-3-chloro-6-(4-chloro-2-fluoro-3-methoxyphenyl)pyridine-2-carboxylate (B1.9),
4-amino-3-chloro-6-(4-chloro-2-fluoro-3-methoxyphenyl)pyridine-2-carboxylic acid triethylammonium salt (B1.10) and
4-amino-3-chloro-6-(4-chloro-2-fluoro-3-methoxyphenyl)pyridine-2-carboxylic acid potassium salt (B1.11)
6-amino-5-chloro-2-(4-chloro-2-fluoro-3-methoxyphenyl)pyrimidine-4-carboxylic acid (B1.12)
methyl 6-amino-5-chloro-2-(4-chloro-2-fluoro-3-methoxyphenyl)pyrimidine-4-carboxylate (B1.13)
ethyl 6-amino-5-chloro-2-(4-chloro-2-fluoro-3-methoxyphenyl)pyrimidine-4-carboxylate (B1.14)
n-propyl 6-amino-5-chloro-2-(4-chloro-2-fluoro-3-methoxyphenyl)pyrimidine-4-carboxylate (B1.15)
i-propyl 6-amino-5-chloro-2-(4-chloro-2-fluoro-3-methoxyphenyl)pyrimidine-4-carboxylate (B1.16)
n-butyl 6-amino-5-chloro-2-(4-chloro-2-fluoro-3-methoxyphenyl)pyrimidine-4-carboxylate (B1.17)
2-butyl 6-amino-5-chloro-2-(4-chloro-2-fluoro-3-methoxyphenyl)pyrimidine-4-carboxylate (B1.18)
tert-butyl 6-amino-5-chloro-2-(4-chloro-2-fluoro-3-methoxyphenyl)pyrimidine-4-carboxylate (B1.19)
allyl 6-amino-5-chloro-2-(4-chloro-2-fluoro-3-methoxyphenyl)pyrimidine-4-carboxylate (B1.20)
2-butoxyethyl 6-amino-5-chloro-2-(4-chloro-2-fluoro-3-methoxyphenyl)pyrimidine-4-carboxylate (B1.21)
6-amino-5-chloro-2-(4-chloro-2-fluoro-3-methoxyphenyl)pyrimidine-4-carboxylic acid triethylammonium salt (B1.22), and/or
6-amino-5-chloro-2-(4-chloro-2-fluoro-3-methoxyphenyl)pyrimidine-4-carboxylic acid potassium salt (B1.23).

9. The herbicide combination as claimed in claim 8, wherein the active ingredient (B) is selected from 4-amino-3-chloro-6-(4-chloro-2-fluoro-3-methoxyphenyl)pyridine-2-carboxylic acid (B1.0) and/or methyl 4-amino-3-chloro-6-(4-chloro-2-fluoro-3-methoxyphenyl)pyridine-2-carboxylate (B1.1).

10. The herbicide combination as claimed in claim 8, wherein said active ingredient (B) is selected from 6-amino-5-chloro-2-(4-chloro-2-fluoro-3-methoxyphenyl)pyrimidine-4-carboxylic acid (B1.12) and/or methyl 6-amino-5-chloro-2-(4-chloro-2-fluoro-3-methoxyphenyl)pyrimidine-4-carboxylate (B1.13).

11. The herbicide combination as claimed in claim 1, wherein the active ingredient (B) is methyl 4-amino-3-chloro-6-(4-chloro-2-fluoro-3-methoxyphenyl)pyridine-2-carboxylate (B1.1).

12. The herbicide combination as claimed in claim 1, wherein said component (C) is selected from the group consisting of trifluralin (C1.1), metribuzin (C1.2), clomazone (C1.3), pendimethalin (C1.4), metolachlor/S-metolachlor (C1.5), flumetsulam (C1.6), alachlor (C1.8), sulfentrazone (C1.10), norflurazon (C1.13), flumioxazin (C1.15), imazapyr/imazapyr-isopropylammonium (C1.16), imazamox/imazamox-ammonium (C1.17), imazaquin/imazaquin-ammonium (C1.18), carfentrazone (C1.20), imazethapyr (C1.21), dicamba (C1.22), mesotrione (C1.23), pyrasulfutole (C1.26), tembotrione (C1.27), sulcotrione (C1.29), bentazone (C2.2), thifensulfuron (C2.3), oxyfluorfen (C2.4), lactofen (C2.5), fomesafen (C2.6), flumiclorac (C2.7), acifluorfen and the sodium salt thereof (C2.8), 2,4-D (C2.10), chlorimuron/chlorimuron-ethyl (C2.11), cloransulam/cloransulam-methyl (C2.12), sethoxydim (C3.1), cycloxydim (C3.2), clethodim (C3.3), quizalofop-P and the ethyl or tefuryl ester thereof (C4.1), fenoxaprop-P and the ethyl ester thereof (C4.2), fluazifop-P and the butyl ester thereof (C4.3), haloxyfop/haloxyfop-P and the methyl or ethyl ester thereof (C4.4), propaquizafop (C4.5), and paraquat/paraquat dichloride (C5.1).

13. The herbicide combination as claimed in claim 11, wherein said component (C) is selected from the group consisting of trifluralin (C1.1), metribuzin (C1.2), clomazone (C1.3), pendimethalin (C1.4), metolachlor/S-metolachlor (C1.5), alachlor (C1.8), sulfentrazone (C1.10), norflurazon (C1.13), flumioxazin (C1.15), imazamox/imazamox-ammonium (C1.17), carfentrazone (C1.20), dicamba (C1.22), mesotrione (C1.23), pyrasulfutole (C1.26), tembotrione (C1.27), sulcotrione (C1.29), bentazone (C2.2), thifensulfuron (C2.3), oxyfluorfen (C2.4), lactofen (C2.5), fomesafen (C2.6), flumiclorac (C2.7), acifluorfen and the sodium salt thereof (C2.8), 2,4-D (C2.10), chlorimuron/chlorimuron-ethyl (C2.11), cloransulam/cloransulam-methyl (C2.12), and clethodim (C3.3).

14. A method of controlling weeds in soybean and/or leguminous species, comprising applying a combination as claimed in claim 1.

15. An active ingredient composition comprising glufosinate-ammonium and, as active ingredient (B), a compound selected from:
- 4-amino-3-chloro-6-(4-chloro-2-fluoro-3-methoxyphenyl)pyridine-2-carboxylic acid (B1.0),
- methyl 4-amino-3-chloro-6-(4-chloro-2-fluoro-3-methoxyphenyl)pyridine-2-carboxylate (B1.1),
- ethyl 4-amino-3-chloro-6-(4-chloro-2-fluoro-3-methoxyphenyl)pyridine-2-carboxylate (B1.2),
- n-propyl 4-amino-3-chloro-6-(4-chloro-2-fluoro-3-methoxyphenyl)pyridine-2-carboxylate (B1.3),
- i-propyl 4-amino-3-chloro-6-(4-chloro-2-fluoro-3-methoxyphenyl)pyridine-2-carboxylate (B1.4),
- n-butyl 4-amino-3-chloro-6-(4-chloro-2-fluoro-3-methoxyphenyl)pyridine-2-carboxylate (B1.5),
- 2-butyl 4-amino-3-chloro-6-(4-chloro-2-fluoro-3-methoxyphenyl)pyridine-2-carboxylate (B1.6),
- tert-butyl 4-amino-3-chloro-6-(4-chloro-2-fluoro-3-methoxyphenyl)pyridine-2-carboxylate (B1.7),
- allyl 4-amino-3-chloro-6-(4-chloro-2-fluoro-3-methoxyphenyl)pyridine-2-carboxylate (B1.8),
- 2-butoxyethyl 4-amino-3-chloro-6-(4-chloro-2-fluoro-3-methoxyphenyl)pyridine-2-carboxylate (B1.9),
- 4-amino-3-chloro-6-(4-chloro-2-fluoro-3-methoxyphenyl)pyridine-2-carboxylic acid triethylammonium salt (B1.10) and
- 4-amino-3-chloro-6-(4-chloro-2-fluoro-3-methoxyphenyl)pyridine-2-carboxylic acid potassium salt (B1.11)
- 6-amino-5-chloro-2-(4-chloro-2-fluoro-3-methoxyphenyl)pyrimidine-4-carboxylic acid (B1.12)
- methyl 6-amino-5-chloro-2-(4-chloro-2-fluoro-3-methoxyphenyl)pyrimidine-4-carboxylate (B1.13)
- ethyl 6-amino-5-chloro-2-(4-chloro-2-fluoro-3-methoxyphenyl)pyrimidine-4-carboxylate (B1.14)
- n-propyl 6-amino-5-chloro-2-(4-chloro-2-fluoro-3-methoxyphenyl)pyrimidine-4-carboxylate (B1.15)
- i-propyl 6-amino-5-chloro-2-(4-chloro-2-fluoro-3-methoxyphenyl)pyrimidine-4-carboxylate (B1.16)
- n-butyl 6-amino-5-chloro-2-(4-chloro-2-fluoro-3-methoxyphenyl)pyrimidine-4-carboxylate (B1.17)
- 2-butyl 6-amino-5-chloro-2-(4-chloro-2-fluoro-3-methoxyphenyl)pyrimidine-4-carboxylate (B1.18)
- tert-butyl 6-amino-5-chloro-2-(4-chloro-2-fluoro-3-methoxyphenyl)pyrimidine-4-carboxylate (B1.19)
- ally 16-amino-5-chloro-2-(4-chloro-2-fluoro-3-methoxyphenyl)pyrimidine-4-carboxylate (B1.20)
- 2-butoxyethyl 6-amino-5-chloro-2-(4-chloro-2-fluoro-3-methoxyphenyl)pyrimidine-4-carboxylate (B1.21) and
- 6-amino-5-chloro-2-(4-chloro-2-fluoro-3-methoxyphenyl)pyrimidine-4-carboxylic acid triethylammonium salt (B1.22) and/or
- 6-amino-5-chloro-2-(4-chloro-2-fluoro-3-methoxyphenyl)pyrimidine-4-carboxylic acid potassium salt (B1.23), and as active ingredient (C), a herbicide selected from the group consisting of trifluralin (C1.1), metribuzin (C1.2), clomazone (C1.3), pendimethalin (C1.4), metolachlor/S-metolachlor (C1.5), flumetsulam (C1.6), dimethenamid/dimethenamid-p (C1.7), alachlor (C1.8), sulfentrazone (C1.10), ethalfluralin (C1.11), norflurazon (C1.13), flumioxazin (C1.15), imazapyr/imazapyr-isopropylammonium (C1.16), imazamox/imazamox-ammonium (C1.17), imazaquin/imazaquin-ammonium (C1.18), carfentrazone (C.1.20), imazethapyr/imazethapyr-ammonium (C.1.21), dicamba (C.1.22), mesotrione (C.1.23), pyrasulfutole (C.1.26), tembotrione (C.1.27), isoxaflutole (C.1.28), sulcotrione (C.1.29), bentazone (C2.2), thifensulfuron (C2.3), oxyfluorfen (C2.4), lactofen (C2.5), fomesafen (C2.6), flumiclorac (C2.7), acifluorfen and the sodium salt thereof (C2.8), 2,4-DB (C2.9), 2,4-D (C2.10) chlorimuron/chlorimuron-ethyl (C2.11), cloransulam/cloransulam-methyl (C2.12), diclosulam (2.13), oxasulfuron (C2.15), sethoxydim (C3.1), cycloxydim (C3.2), clethodim (C3.3), quizalofop-P and the ethyl or tefuryl ester thereof (C4.1), fenoxaprop-P and the ethyl ester thereof (C4.2), fluazifop-P and the butyl ester thereof (C4.3), haloxyfop/haloxyfop-P and the methyl or ethyl ester thereof (C4.4), propaquizafop (C4.5), and paraquat/paraquat dichloride (C5.1), wherein said combination exhibits herbicide efficacy greater than expected for combinations of component (C) with mixture of components (A) and (B)

and wherein the soybean species is tolerant to the herbicides (A), (B), and (C) present in combination.

16. The active ingredient composition as claimed in claim 15, wherein said active ingredient (B) is selected from 4-amino-3-chloro-6-(4-chloro-2-fluoro-3-methoxyphenyl)pyridine-2-carboxylic acid (B1.0) and/or methyl 4-amino-3-chloro-6-(4-chloro-2-fluoro-3-methoxyphenyl)pyridine-2-carboxylate (B1.1).

17. The active ingredient composition as claimed in claim 15, wherein said active ingredient (B) is selected from 6-amino-5-chloro-2-(4-chloro-2-fluoro-3-methoxyphenyl)pyrimidine-4-carboxylic acid (B1.12) and/or methyl 6-amino-5-chloro-2-(4-chloro-2-fluoro-3-methoxyphenyl)pyrimidine-4-carboxylate (B1.13).

18. The active ingredient composition as claimed in claim 15, further comprising a safener.

* * * * *